United States Patent [19]

Hirsch et al.

[11] Patent Number: 5,368,599
[45] Date of Patent: Nov. 29, 1994

[54] SUGICAL FASTENING APPARATUS WITH SUTURE ARRAY

[75] Inventors: Leon C. Hirsch; David T. Green, both of Westport; Henry Bolanos, East Norwalk, all of Conn.; Wayne P. Young, Brewster, N.Y.; Dominick L. Mastri, Bridgeport, Conn.; Lisa W. Heaton, Norwalk, Conn.; Mark E. Alari, Derby, Conn.

[73] Assignee: United States Surgical Corporation, Norwalk, Conn.

[21] Appl. No.: 958,392

[22] Filed: Oct. 8, 1992

[51] Int. Cl.⁵ .............................................. A61B 17/00
[52] U.S. Cl. .................................. 606/139; 606/144; 227/175; 227/176; 227/180; 227/181
[58] Field of Search ........................... 606/69–71, 606/75, 139, 142, 143, 144, 148, 150, 151, 213, 215, 216, 220, 221; 227/175–178, 180, 181, 901, 19; 128/898

[56] References Cited

U.S. PATENT DOCUMENTS

| | | |
|---|---|---|
| 1,577,054 | 3/1926 | Berkmann . |
| 2,387,131 | 10/1945 | Fernandez .......................... 606/216 |
| 4,016,884 | 4/1977 | Kwan-Gett ......................... 606/151 |
| 4,232,810 | 11/1980 | Russell . |
| 4,310,115 | 1/1982 | Inoue . |
| 4,354,628 | 10/1982 | Green . |
| 4,414,908 | 11/1983 | Eguchi et al. . |
| 4,417,532 | 11/1983 | Yasukata . |
| 4,440,171 | 4/1984 | Nomato et al. . |
| 4,465,070 | 8/1984 | Eguchi . |
| 4,506,671 | 3/1985 | Green . |
| 4,512,346 | 4/1985 | Lemale . |
| 4,519,392 | 5/1985 | Lingua ............................... 606/157 |
| 4,553,544 | 11/1985 | Nomoto et al. . |
| 4,593,843 | 10/1986 | Saravis . |
| 4,665,916 | 5/1987 | Green . |
| 4,702,250 | 10/1987 | Ovil et al. ......................... 606/148 |
| 4,703,887 | 11/1987 | Clanton et al. . |
| 4,747,358 | 5/1988 | Moll et al. . |
| 4,749,114 | 6/1988 | Green ................................ 227/19 |
| 4,753,237 | 6/1988 | Puchy . |
| 4,754,758 | 7/1988 | Li .................................... 606/213 |
| 4,773,420 | 9/1988 | Green . |
| 4,777,949 | 10/1988 | Perlin ................................ 24/546 |
| 4,817,847 | 4/1989 | Redtenbacher et al. . |
| 4,819,853 | 4/1989 | Green . |
| 4,821,939 | 4/1989 | Green ................................ 227/19 |
| 4,881,545 | 11/1989 | Issacs et al. . |
| 4,889,110 | 12/1989 | Galline et al. ..................... 606/69 |
| 4,890,612 | 1/1990 | Kensey . |
| 4,930,674 | 6/1990 | Barak ................................ 227/180 |
| 4,961,741 | 10/1990 | Hayhurst . |
| 5,005,749 | 4/1991 | Aranyi . |
| 5,005,754 | 4/1991 | Van Overloop . |
| 5,037,021 | 8/1991 | Mills et al. . |
| 5,047,047 | 9/1991 | Yoon . |
| 5,059,201 | 10/1991 | Asnis . |
| 5,100,042 | 3/1992 | Gravener . |
| 5,108,421 | 4/1992 | Fowler . |
| 5,116,349 | 5/1992 | Aranyi . |
| 5,129,912 | 7/1992 | Noda et al. . |
| 5,137,198 | 8/1992 | Nobis et al. ...................... 227/19 |
| 5,179,964 | 1/1993 | Cook . |
| 5,188,636 | 2/1993 | Fedotov ............................ 606/139 |
| 5,242,457 | 9/1993 | Akapov et al. . |
| 5,263,629 | 11/1993 | Trumbull et al. .................. 606/151 |

OTHER PUBLICATIONS

"United States Surgical Corporation Information Booklet for Auto Suture ® Purse String Instrument", Copyright 1977, 1978, United States Surgical Corporation.
Article reprinted from Contemporary OB/GYN, Aug. 1991, describing the use of surgical staplers for Cesarean sections.
Brochure regarding Surgical Stapling Techniques in performing Cesarean sections.

Primary Examiner—Stephen C. Pellegrino
Assistant Examiner—Jeffrey A. Schmidt

[57] ABSTRACT

An apparatus for simultaneously applying to body tissue at least one surgical suture in conjunction with a plurality of surgical fasteners arranged end to end in rows. The apparatus preferably includes a knife for making an incision in the body tissue sealed in each side by at least one row of fasteners. The fasteners are two-part fasteners fabricated from bioabsorbable material. The incision is closed by pulling the ends of the suture(s).

63 Claims, 16 Drawing Sheets

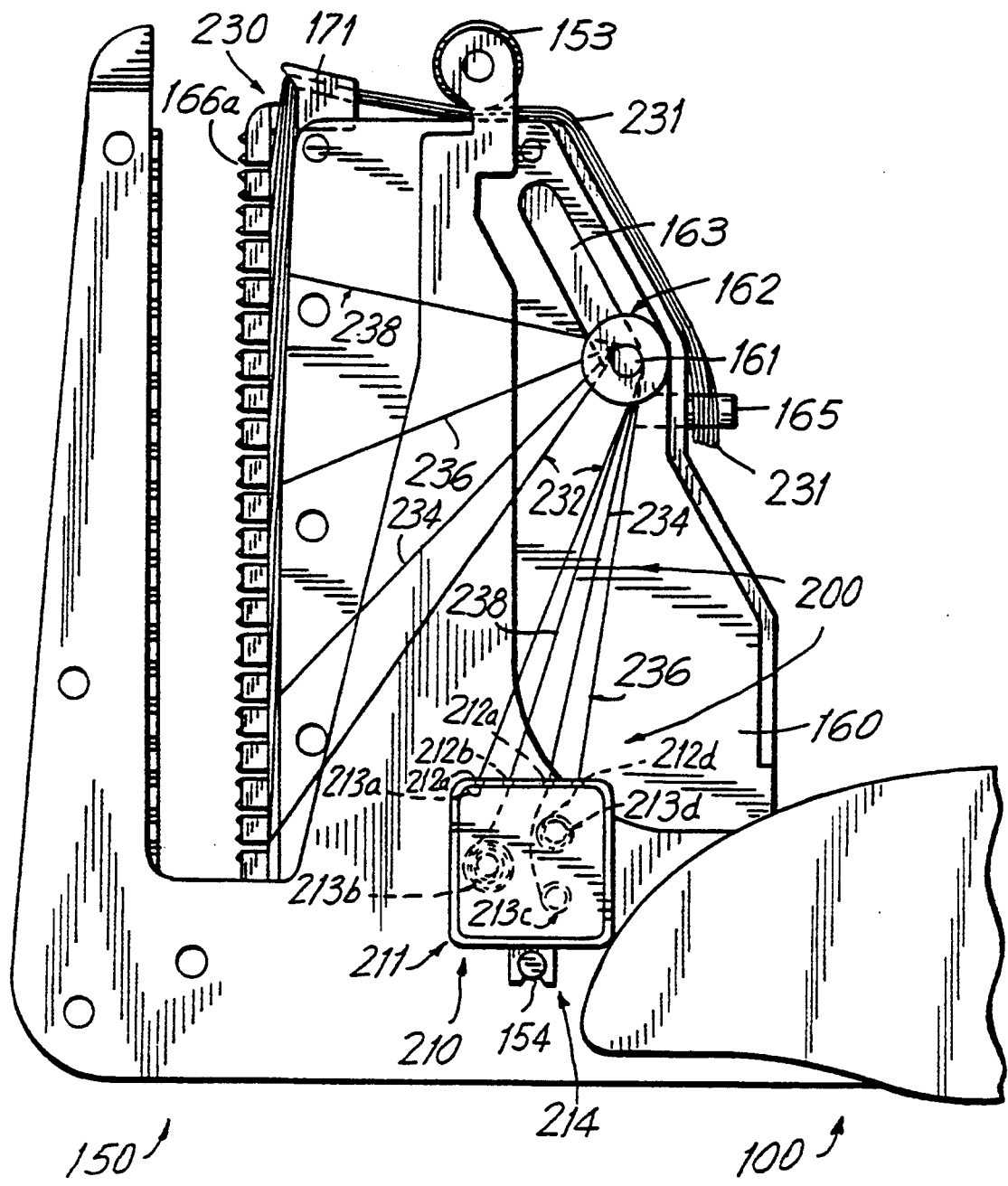

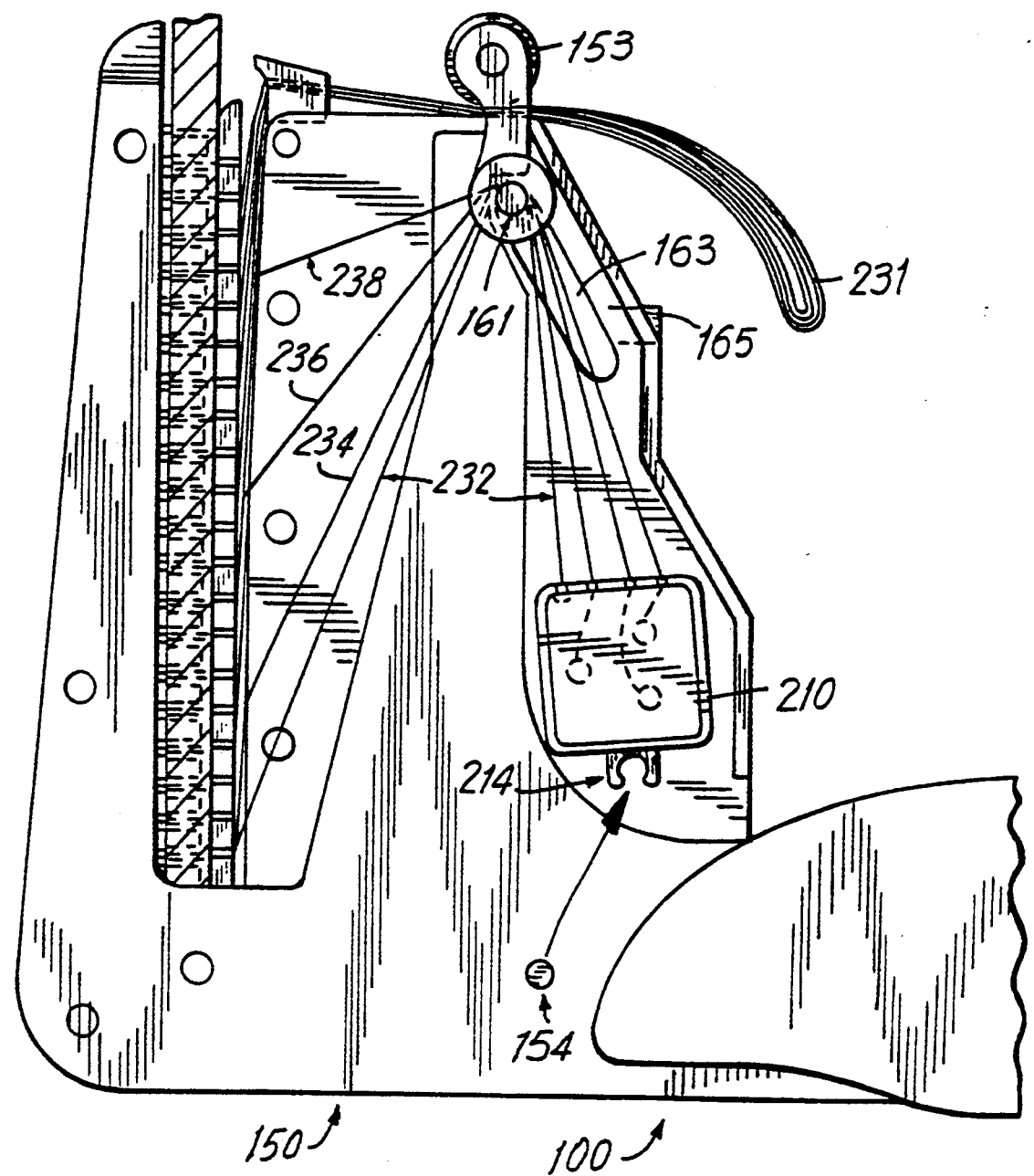

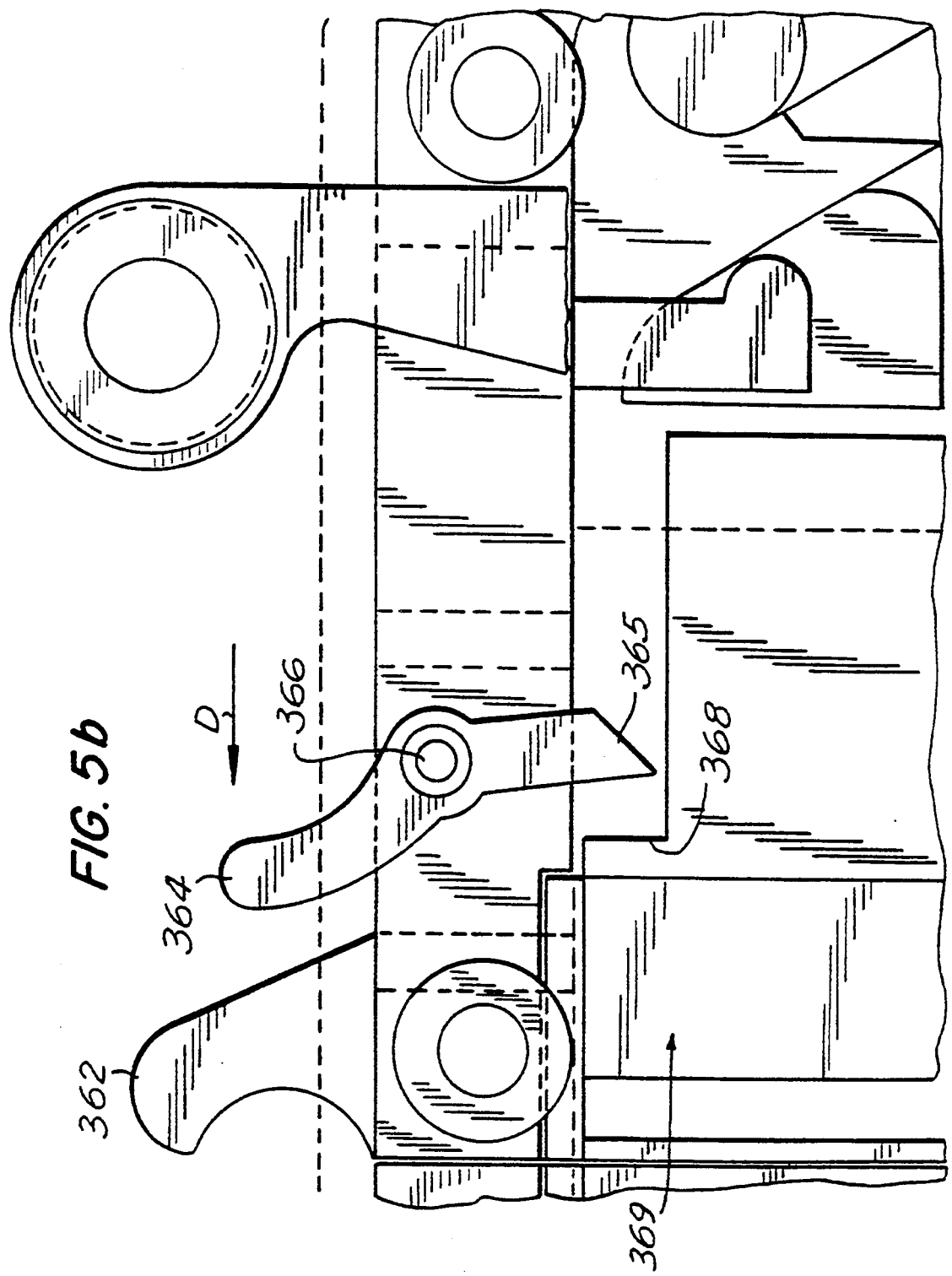

SUGICAL FASTENING APPARATUS WITH SUTURE ARRAY

BACKGROUND OF THE INVENTION

1. Field of the Invention

The present invention relates to an apparatus for applying surgical fasteners to body tissue, and more particularly to an apparatus which applies a suture array in conjunction with the surgical fasteners.

2. Background of the Art

It is well known that surgical stapling, as compared to suturing, requires less tissue manipulation, reduces blood loss, and reduces trauma to the patient. The faster wound closure and reduced operative time resulting from surgical stapling reduces patient anesthesia requirements and the possibility of inflammation and infection.

Various types of instruments for applying surgical staples are known. Several of these instruments, such as that disclosed in U.S. Pat. No. 4,354,628, have a cartridge jaw containing two or more rows of metal staples and an anvil jaw having a corresponding number of depressions. In an operation, the anvil and cartridge jaws are approximated to clamp tissue therebetween, and the instrument handle is actuated to fire the rows of staples simultaneously through the tissue and against the anvil where they are crimped into a B-shaped configuration.

Instruments for simultaneously applying two or more rows of two pare fasteners are also currently in use. These fasteners comprise a tissue piercing fastener portion and a receiver portion, both of which are composed of materials which are totally absorbed by the body. The instruments operate similarly to those which apply metal staples in that the fastener holding jaw and receiver holding jaw are approximated, and the instrument handle is subsequently actuated to force the fastener portions through the tissue and into interlocking arrangement with the corresponding receivers. The instruments may also include a knife positioned between the rows of fasteners, such as in U.S. Pat. Nos. 4,665,916 and 5,116,349, both of which are herein incorporated by reference. The knife creates an incision in tissue as the fasteners are applied to the tissue.

The instruments described above may be used in abdominal surgery for the removal or repair of organs, in gynecological surgery such as performing cesarean sections, and in many other types of operations which are familiar to those with skill in the surgical arts.

In certain types of procedures, such as joining tubular tissue, a suture is employed as a "purse string" to manipulate the tissue to facilitate the joining procedure. Instruments to apply a suture to body tissue in conjunction with metal staples arranged side to side are known and described in U.S. Pat. Nos. 4,749,114; 4,773,420; and 4,821,939. The sutures in these instruments are placed around the tissue structure and tightened, i.e. pulled, to compress the tissue.

There exists a need for an improved instrument to apply arrayed suture(s), in conjunction with one piece staples or with two-part surgical fasteners. Such instrument would have broader applications than the purse string instrument discussed above as it could function to place sutures in conjunction with fasteners adjacent an incision, thereby enabling quick closure of the incision by tightening the sutures.

One application for such an improved instrument would be in hysterotomy procedures. Hysterotomy procedures performed in cesarean sections are now performed with a surgical fastener applying apparatus such as described in U.S. Pat. No. 5,116,349. This instrument, which is capable of making an incision in tissue and simultaneously applying at least one row of two-part bioabsorbable fasteners to the tissue on each side of the incision, provided a marked advance in obstetrical surgery as it reduced infection rate, reduced blood loss, and controlled uterine opening to facilitate delivery of the baby. The fasteners helped to minimize the amount of bleeding by creating a hemostatic seal along the edges of the incised tissue.

After the hysterotomy has been performed with this instrument, and the baby delivered through the incision, surgeons close the incision by passing a suture between the backspan and retainer portions of the fasteners while stitching across the incision. The suture is tugged slightly to cinch the suture. The procedure is repeated with the suture running back and forth across the incision through each of the fasteners until the sides of the incision are drawn into close juxtaposition.

Although stitching the incision by hand with a needle and suture is effective in closing the wound, this procedure is time consuming because the suture has to be passed individually through each of the fasteners. Additionally, the required repeated manipulation of the needle increases the likelihood of doctors sticking themselves with needles. Moreover, in manual suturing, wound closure can vary with the skills of the particular surgeon. It would be advantageous to provide an instrument which can eliminate these disadvantages and shorten the time period involved in suturing since this would not only reduce blood loss and trauma to the patient, but would reduce hospital costs. Such an instrument would have applications beyond hysterotomy procedures as it would enable placement of sutures in conjunction with fasteners to expedite wound closure. Up to now, there has been no instrument for accomplishing this stitching function automatically.

SUMMARY OF THE INVENTION

The present invention advantageously provides an apparatus which can simultaneously apply fasteners and one or more sutures to the body tissue to thereby facilitate and expedite wound closure.

The surgical fastener applying apparatus of the present invention includes a frame, a cartridge mounted to the frame for holding a plurality of surgical fasteners in at least two rows, and means for applying the surgical fasteners to body tissue. The individual fasteners in each row are preferably oriented in end to end fashion. The applying means simultaneously applies at least one, and preferably up to four, suture(s) in conjunction with the fasteners, such that a portion of the suture extends across the rows from a fastener on one of said rows to a fastener on another of said rows.

The surgical fasteners are preferably of two part construction and are fabricated from a bioabsorbable material such as homopolymers and copolymers of glycolide, lactide, dioxanone, caprolactone, trimethylene carbonate and blends thereof. The suture is also preferably composed of bioabsorbable materials. Alternatively, the fasteners can be an integral single piece construction such as metal staples.

The cartridge for holding the fasteners includes a tissue contacting face, the portion of the suture extending across the rows being at least partially positioned in a loop located away from the tissue contacting face. Means may be included for releasably holding the loop until the fasteners are applied.

The ends of the suture(s) may be anchored to the apparatus by tensioned rotatable spools contained in a housing releasable from the apparatus when the fasteners are fired.

BRIEF DESCRIPTION OF THE DRAWINGS

FIG. 2 is a side elevational view of the distal end of the apparatus in a preapproximated position.

FIGS. 4a and 4b are, respectively, elevational and sectional views of the distal end of the apparatus in approximated and fired condition.

FIG. 5b is an enlarged view of the suture retaining member of FIG. 5a showing the apparatus in the fired condition and after the knife has been retracted.

DETAILED DESCRIPTION OF PREFERRED EMBODIMENT

Although the principles of the invention are applicable to other types of surgical stapler apparatus, the invention will be understood clearly from an explanation of its application to the surgical stapler apparatus of the type described in U.S. Pat. No. 5,116,349 mentioned above and hereby incorporated by reference in its entirety. The invention is applicable also to both permanent and disposable apparatus. Accordingly, although the invention will be illustrated in an embodiment in which a cartridge comprising a fastener holder and an anvil assembly is mounted in a disposable instrument, the invention could equally be described in use in a non disposable embodiment.

Figure 1:
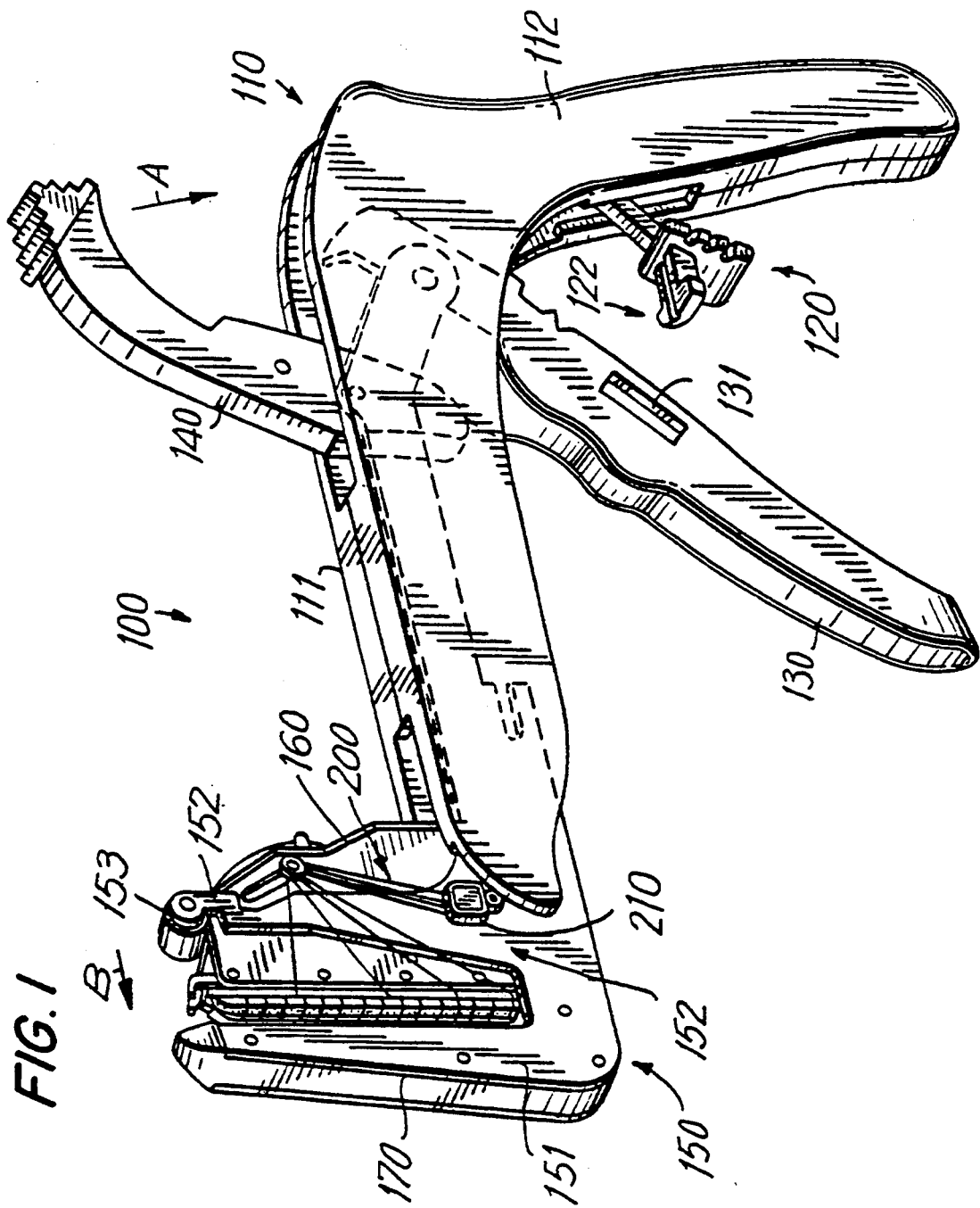
FIG. 1 is a perspective view showing a fastener applying apparatus which includes the suture array of the present invention.

Turning now to FIG. 1 which illustrates a surgical fastener applying apparatus 100, the apparatus includes a body portion 110, having a longitudinally extending portion 111 and a handle 112. The distal portion 150 of body portion 110 is U-shaped and includes distal leg 151 and proximal leg 152.

Cartridge 160 is located at the proximal leg 152 of distal portion 150 of the apparatus and has distal tissue contacting surfaces 166a (FIG. 2) and 166b (not shown) through which the fasteners described below exit. The anvil assembly 170 is fixedly positioned at the distal leg 151 of the U-shaped distal portion 150. Spacer pin 153 is a cross pin which serves to space the left and right frames apart.

Approximating lever 140 is pivotally mounted to the apparatus and controls the approximation or closing of the jaws of the instrument. When the approximating lever 140 is pressed downwardly in the direction of arrow A, the cartridge 160 is distally advanced (arrow B) to come into close contact and clamp the body tissue between the jaws of the instrument.

Trigger 130, which is an actuator for the fastener driving mechanism, is pivotally mounted to the apparatus such that squeezing the trigger 130 effects driving of the fasteners.

Trigger lock 120 is pivotally mounted to the handle 112 and has prongs 122 for snap-fit engagement into slot 131 in the trigger. Once the apparatus is fully fired, the trigger is locked in the actuated position and cannot be refired.

Figure 1A:
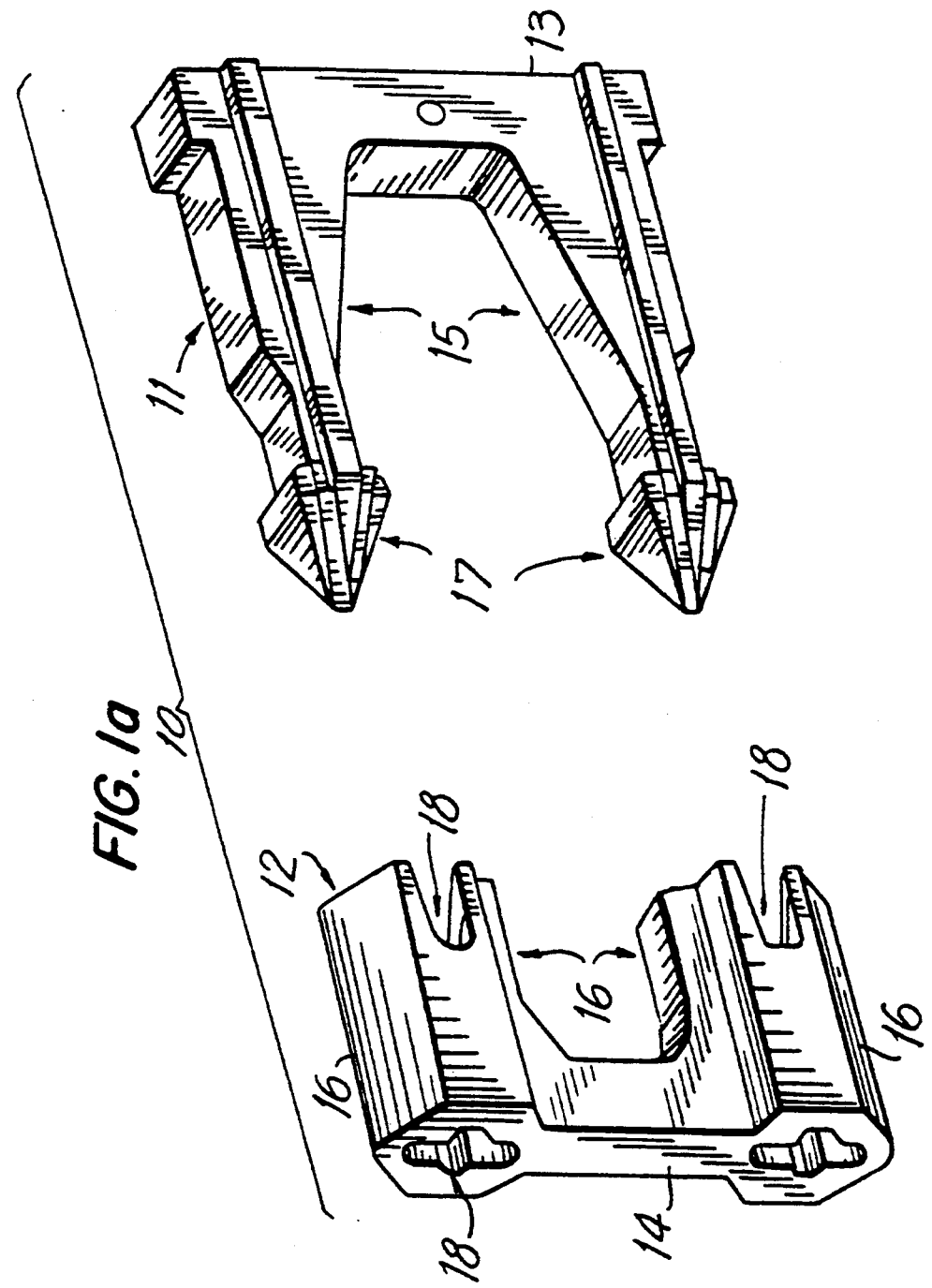
Fig. 1a is an exploded perspective view of a two-part surgical fastener.
Figure 3:
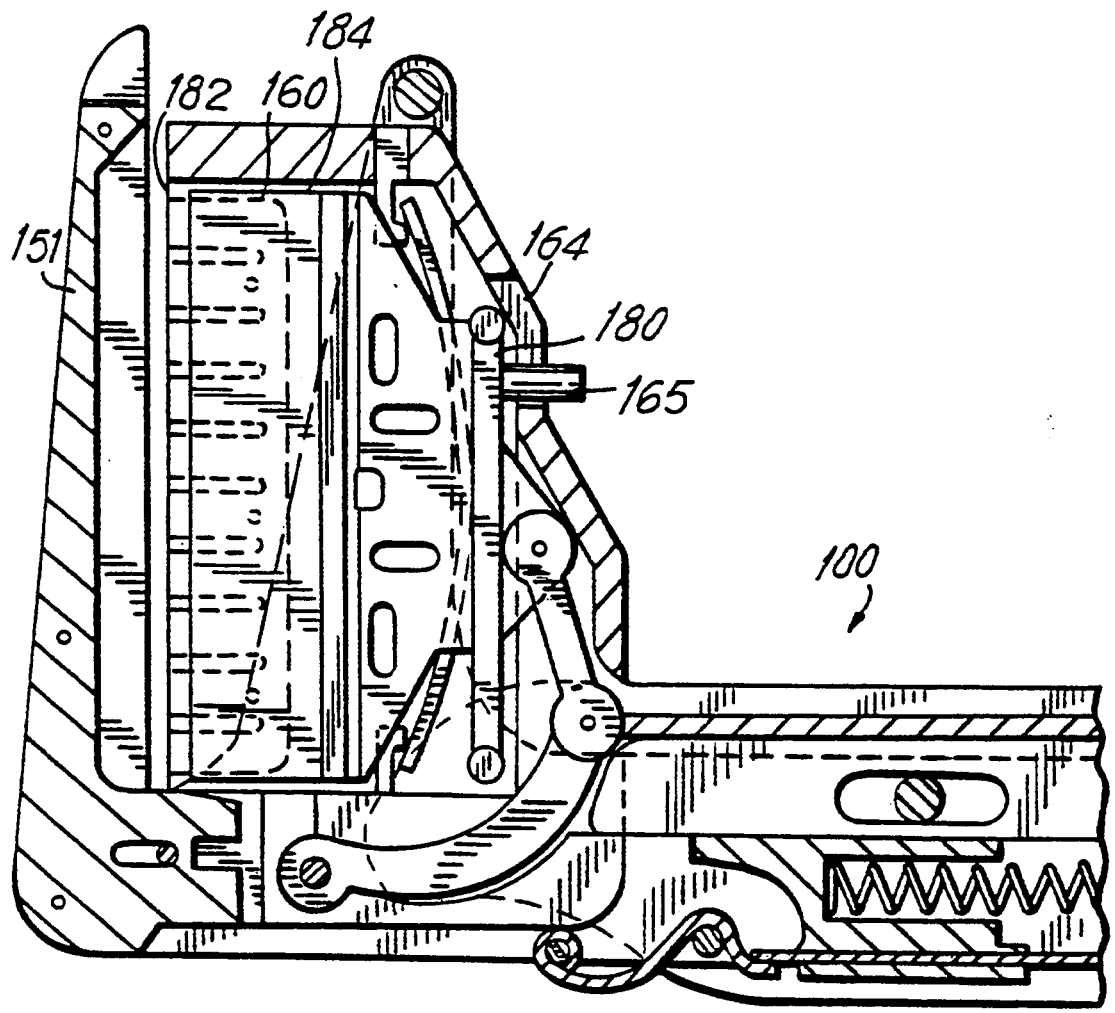
FIG. 3 is a sectional view of the distal end of the apparatus in an approximated and prefired condition.

Contained within the cartridge 160 and anvil assembly are the two-part bioabsorbable fasteners 10, illustrated in FIG. 1A. The fasteners generally comprise a staple or fastener (tissue piercing) portion 11 having a backspan 13 and prongs 15 with barbs 17 at the tips thereof. The fastener portions 11 (referred to herein also as the fasteners) are initially located in slots in the cartridge, each fastener portion 11 being in a separate slot, and the fastener portion 11 being oriented in parallel rows with the fastener portions in each row being oriented in end to end fashion. End to end means that a line defining the extension of the row of fastener portions coincides with a single straight line extending lengthwise through the backspan of each fastener portion in the row.

At least one row of fasteners is positioned on each side of a knife blade such that when the instrument is fired, an incision is made by the knife in body tissue, the tissue being sealed on both sides of the incision by the rows of fasteners. The fasteners are all applied substantially simultaneously with the making of the incision. The retainer portion 12 of the two-part fastener comprises a base 14 with columnar members 16 having apertures 18 for receiving the barbed prongs 15 of the fastener portion 11. Once engaged, the fastener portion and the retainer lock together. It is desirable to fabricate the fasteners from a bioabsorbable material such as polyglycolide, polylactide or copolymers thereof to eliminate the need for removing the fasteners at a later time.

It should be noted that the term "fasteners" as used herein is a generic term including not only the two-part resinous surgical fasteners having a staple shaped fastener portion and an interlocking retainer portion described above, but can also include metal surgical staples as shown in U.S. Pat. No. 4,354,628, which are crimped and can be made of metal, staples composed of polymeric material, and their equivalents. Similarly, the term "anvil assembly" is used herein as a generic term to include the anvil used to clinch metal surgical staples, the retainer holder and retainer member of two-part resinous surgical fasteners, and the equivalent of these elements.

Referring to FIG. 2, the apparatus further includes a suture array assembly 200, which includes two spool boxes 210 and 220 (only spool box 210 is shown) and a suture array 230 comprising sutures 232, 234, 236 and 238. The spool boxes 210 and 220 are mounted at the proximal leg 152 of the apparatus, one spool box on each side of the apparatus.

Spool box 210 includes a housing 211 having a cover (not shown) with four apertures 212a, 212c, 212d, and 212b, each dimensioned to-allow passage of respective sutures 232, 234, 236 238 therethrough. As shown in the drawings, sutures 234, 236 and 238 are wound around spools 213c, 213d and 213a, respectively. Suture 232 is held in spool box 210 at area 213a by a knot or by crimping. Housing 211 includes a pronged catch 214 which is adapted to resiliently engage a laterally projecting pin 154 protruding from proximal leg 152 of the U-shaped distal portion. A pin is positioned on the opposite side of the housing to receive a similar pronged catch of spool box 220 in the same fashion.

Cartridge 160 of the embodiment of FIGS. 1–4, includes a slot 163 to receive pin 161. A relatively wider flat plate 162 is attached to the end of pin 161 to maintain the sutures in contact with pin 161. Loop retaining pin 165 is fixedly attached to cam bar 180 and extends through aperture 164 in the rear of the cartridge (FIG. 3) so as to project at least partially out of the cartridge 160 when the cartridge is in the prefered configuration.

In general, once the instrument is assembled, each of the four sutures 232, 234, 236 and 238 extends from spool box 210, around pin 161, and through the area of the cartridge containing the fasteners. The sutures then exit from the fasteners and extend through anchor post 171, along the top of the cartridge 160 (underneath spacer pin 153) and down along the back of the cartridge 160 where they are looped around (collectively referred to as loop 231) and held in place by anchor 165. The sutures then extend back along the top of the cartridge, through the fasteners and into spool box 220. Note that loop 231 is positioned away from the knife slot 169 of the tissue contacting faces 166a, 166b to prevent the suture portions in the loop from interfering with the incision of the tissue and from being cut by the knife when it emerges from knife slot 169 during firing of the apparatus.

Figure 5A:
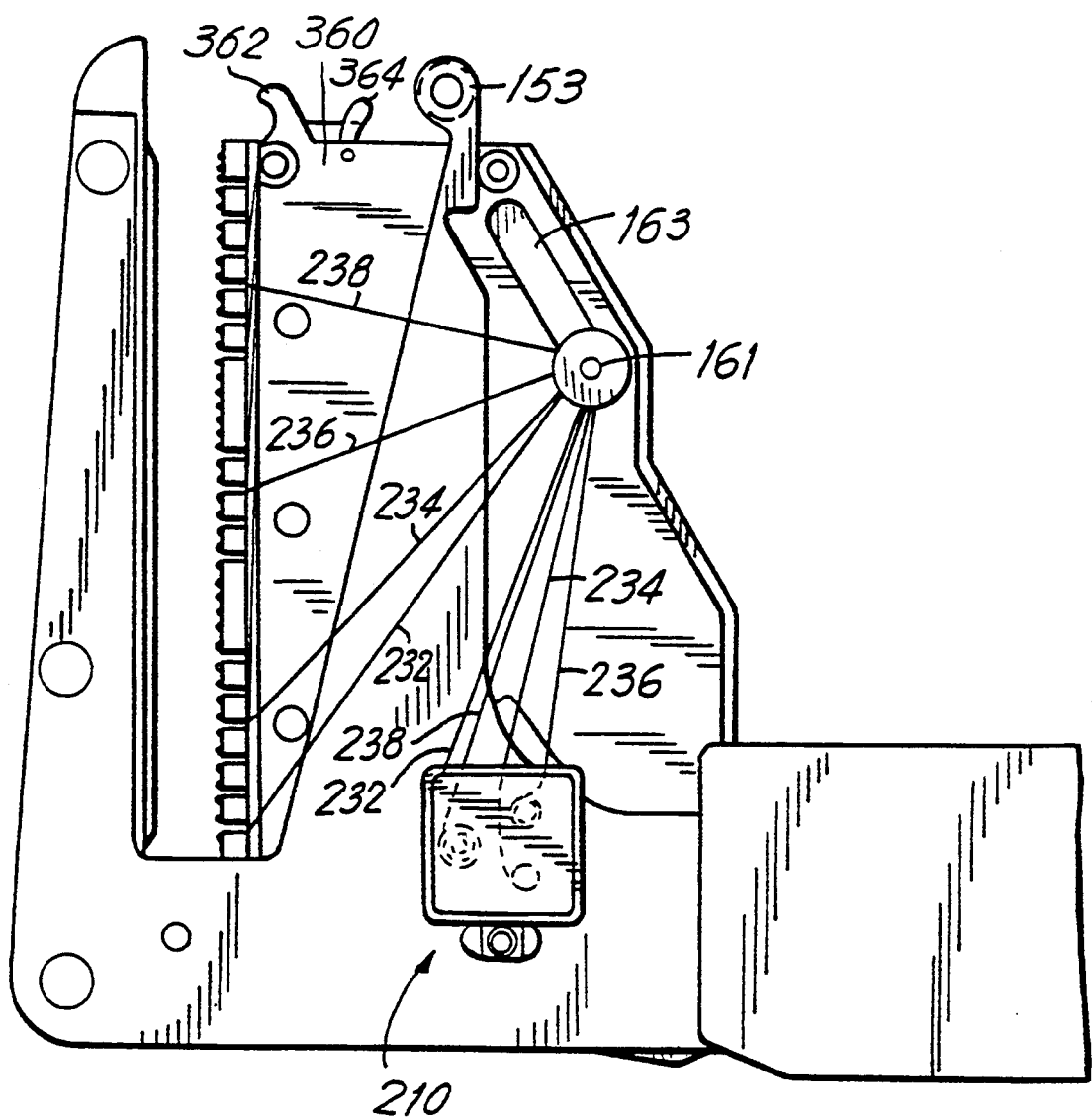
FIG. 5a is a side sectional view of the distal end of an alternate embodiment of the apparatus in a preapproximated position.

In an alternate, preferred, embodiment shown in FIGS. 5a and 5b, the cartridge 360 includes a pair of spaced apart ears 362 (only one of which is shown) and a centrally positioned loop anchor 364. Ears 362 extend upwardly from the top of the cartridge and are fixedly positioned thereon. Loop anchor 364 is pivotably attached at the top of the cartridge by pivot pin 366 for movement to loosen and allow release of the sutures. All four sutures extend from their respective spool boxes, around pin 161 and through the cartridge in the manner described above for the previous embodiment. However, instead of anchor post 171 and anchor 165, the sutures in this embodiment extend through the opening between spaced apart ears 362 and are looped around loop anchor 364. This reduces the extent the sutures travel on the outside of the cartridge. When the instrument is fired, the tension of the sutures will pivot loop anchor 364 distally (arrow D) so that the sutures are no longer tensioned. Upon retraction of the knife 369, anchor 364 is pivoted further distally as step 368 contacts the bottom portion 365 of anchor 364. Thus, anchor 364 does not interfere with retraction of the knife and the non-tensioned position of the sutures is maintained.

The positioning of the sutures with respect to the fastener portions is illustrated in detail in FIGS. 8–12. In these figures, the fastener slots for holding the fasteners are shown without the fasteners for ease of explanation. Note that this description of the position of each individual suture is the route of the suture once the instrument is assembled. The suture may not necessarily be threaded i.e. assembled in this order. For example, each suture can be threaded through its respective fasteners first, and then each end wrapped around the pin and connected to its respective spools in opposing spool boxes.

SUTURE 232

Suture 232 is positioned as follows:

a) through aperture 212a of spool 210 and around pin 161 (FIG. 2);
b) across the side of the cartridge and through the fastener slot 163a in region 167a (corresponding to the approximate mid portion of the backspan of the fastener portion) (FIGS. 8 and 9);
c) a short distance parallel to the central knife slot 169 of the fastener cartridge;
d) through gap 167b between fastener slots 163a and 163b;
e) along the side of the tissue contacting surface 166a (FIGS. 2, 8, 9);
f) along the top of cartridge 160 (through post 171 and under pin 153);
g) down along the back of cartridge 160 and around into loop 231 (held in place by loop retaining pin 165);
h) up the back and along the top of cartridge 160 in the opposite direction;
i) along the side of the tissue contacting face 166b of the cartridge;
j) through gap 168b between fastener slots 163l and 163m;
k) parallel to knife slot 169 and through region 168c of slot 163l;
l) again up along the side of the tissue contacting face 166b of the cartridge and around into loop 231;
m) back over the top of the cartridge, down through tissue contacting face 166a and through gap 167d between fastener slots 163c and 163b;
n) parallel to knife slot 169 and through region 167c of fastener slot 163b;
o) along the side of the tissue contacting face 160 of the cartridge, around into loop 231, back along the top of the cartridge and down through opposing contacting face 166b;
p) through gap 168b between fastener slot 163l and lowermost fastener slot 163k;
q) through region 168a of slot 163k; and
r) around the other side of the cartridge, around pin 161, and down into spool box 220 which is located on the opposite side of the cartridge from spool 210.

SUTURE 234

Figure 8:
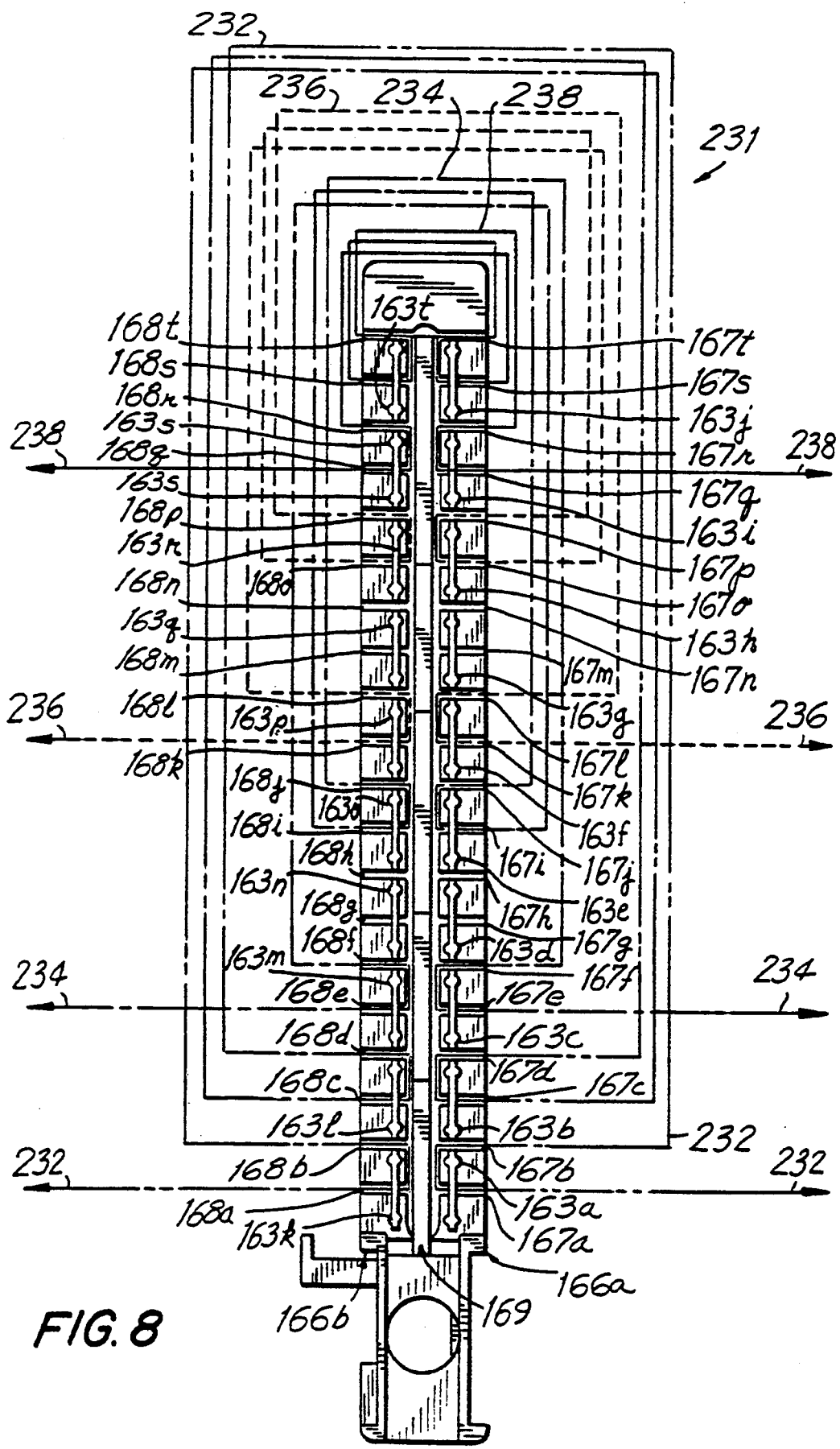
FIG. 8 is a diagrammatic view of the suture array configuration of the present invention.
Figure 9:
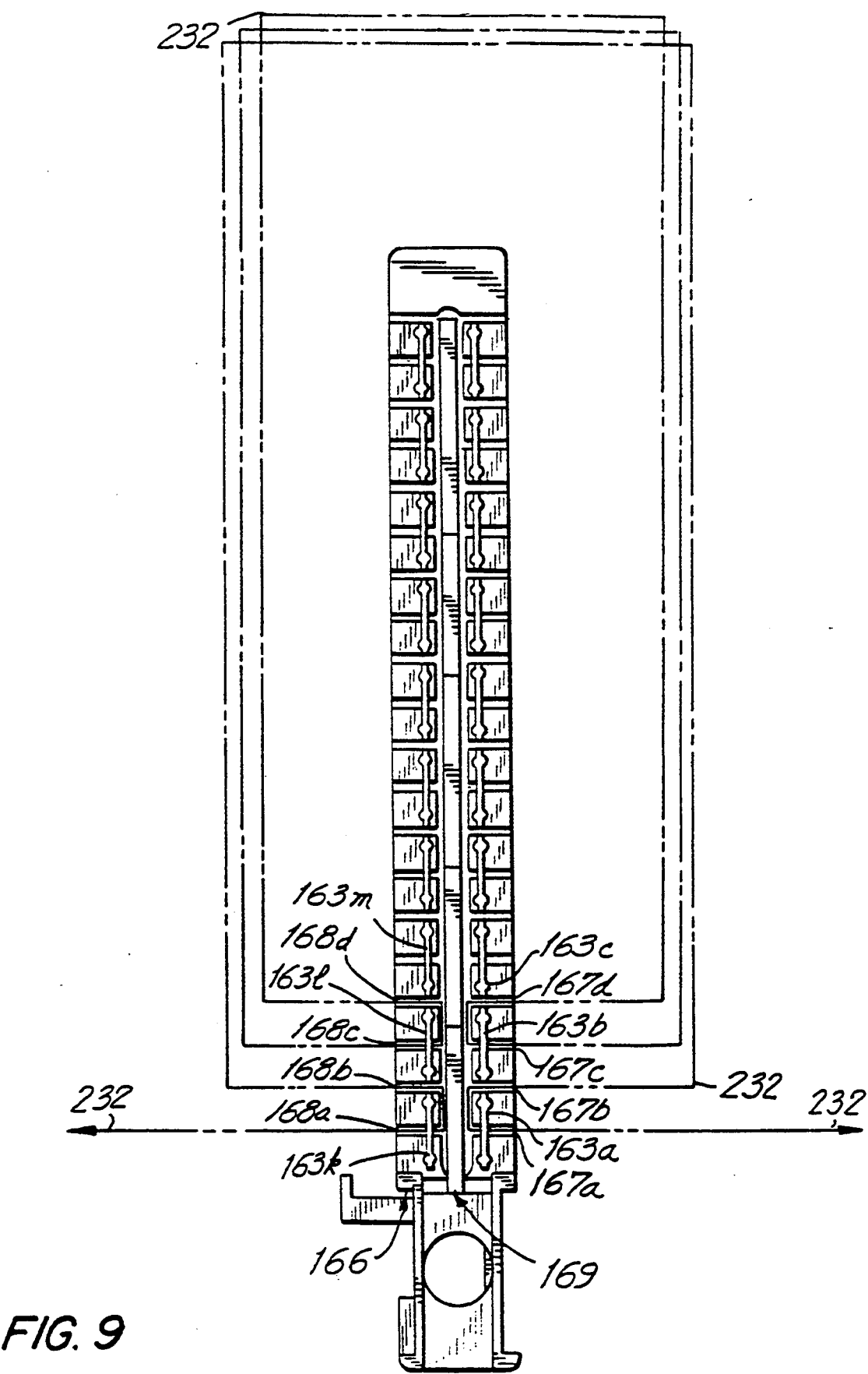
FIGS. 9, 10, 11 and 12 are diagrammative views showing for clarity the configuration of an individual suture of the suture array of FIG. 8.
Figure 10:
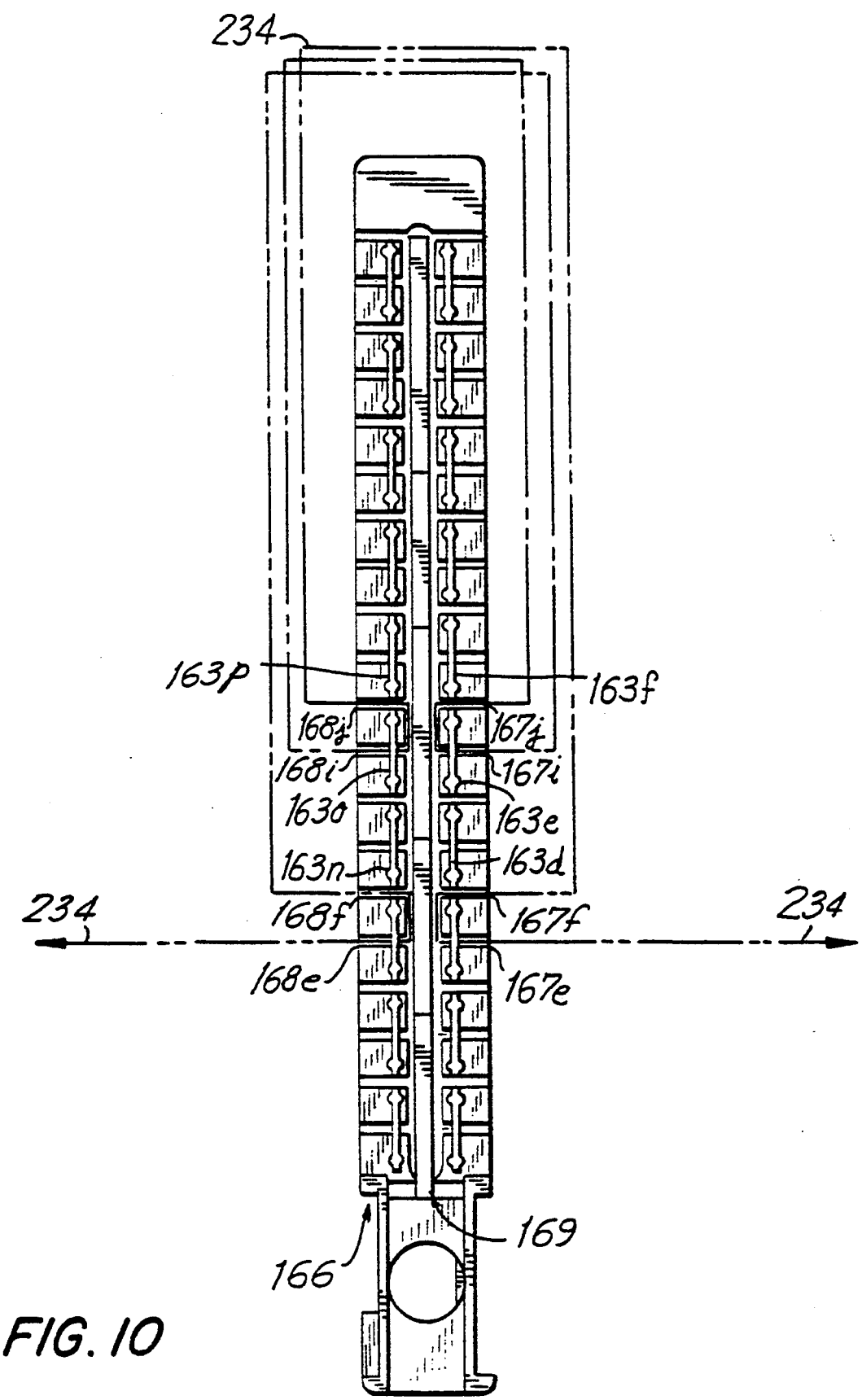

Suture 234 is positioned as follows:

a) through aperture 212c of spool 210 and around pin 161 (FIG. 2);
b) across the side of the cartridge and through the fastener slot 163c in region 167e (corresponding to the approximate mid portion of the backspan of the fastener portion) (FIGS. 8 and 9);
c) a short distance parallel to the central knife slot 169 of the fastener cartridge;
d) through gap 167f between fastener slots 163c and 163d;
e) along the side of the tissue contacting surface 166a (FIGS. 2, 8, 10)

f) along the top of cartridge 160 (through post 171 and under pin 153);

g) down along the back of cartridge 160 and around into loop 231 (held in place by loop retaining pin 165);

h) up the back and along the top of cartridge 160 in the opposite direction;

i) along the side of the tissue contacting face 166*b* of the cartridge;

j) through gap 168*j* between fastener slots 163*o* and 163*p*;

k) parallel to knife slot 169 and through region 168*i* of slot 163*o*;

l) again up along the side of the tissue contacting face 166*b* of the cartridge and around into loop 231;

m) back over the top of the cartridge, down through tissue contacting face 166*a* and through gap 167*j* between fastener slots 163*f* and 163*e*;

n) parallel to knife slot 169 and through region 167*i* of fastener slot 163*e*;

o) along the side of the tissue contacting face of the cartridge, around into loop 231, back along the top of the cartridge and down through opposing contacting face 166*b*;

p) through gap 168*f* between fastener slots 163*m* and 163*n*;

q) through region 168*e* of slot 163*m*; and r) around the other side of the cartridge, around pin 161, and down
into spool box 220 which is located on the opposite side of the cartridge from spool box 210.

Suture 236

Figure 11:
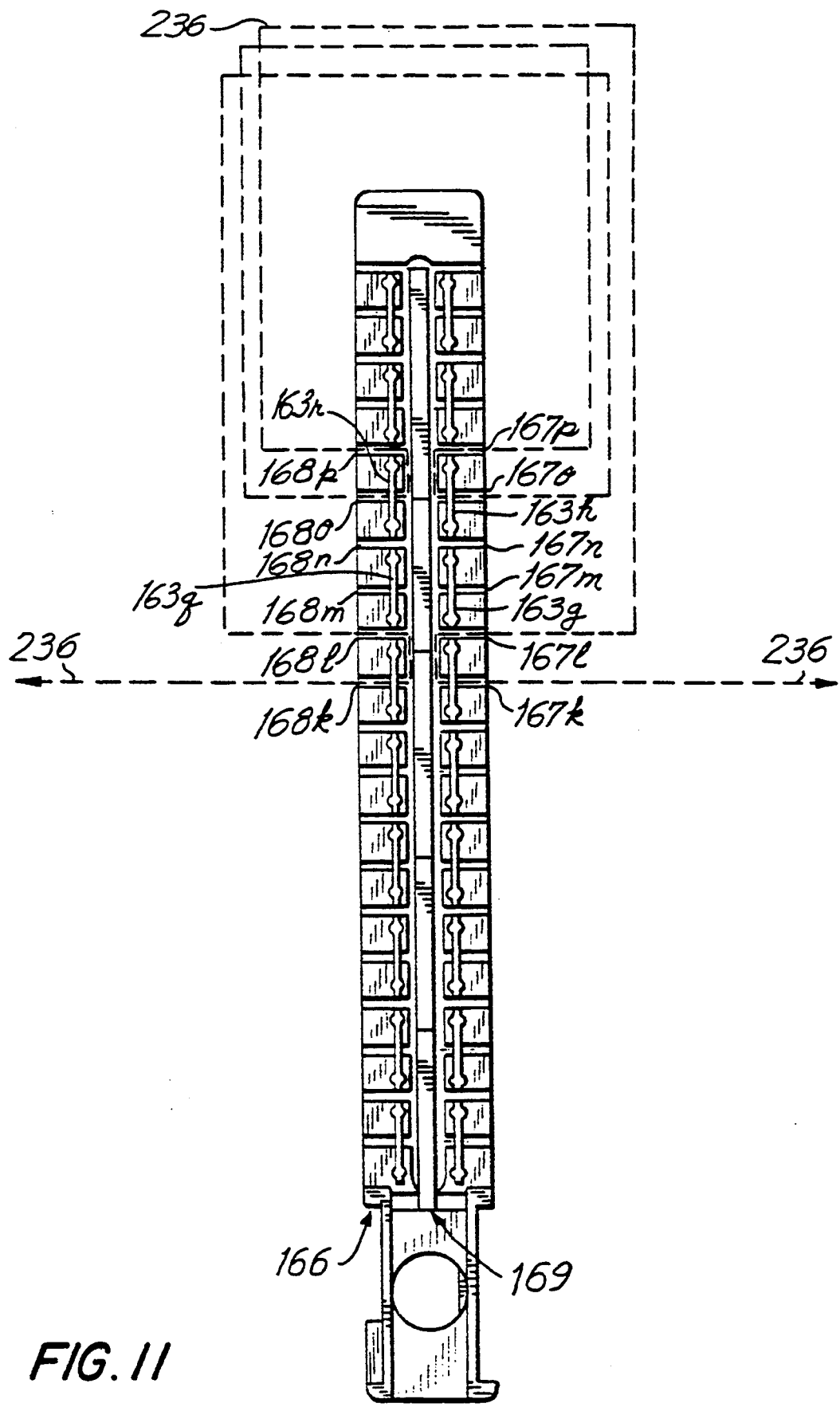

Suture 236 is positioned as follows:

a) through aperture 212*d* of spool 210 and around pin 161 (FIG. 2);

b) across the side of the cartridge and through the fastener slot 163*f* in region 167*k* (corresponding to the approximate mid portion of the backspan of the fastener portion) (FIGS. 8 and 11);

c) a short distance parallel to the central knife slot of the fastener cartridge;

d) through gap 167*l* between fastener slots 163*f* and 163*g*;

e) along the side of the tissue contacting surface 166*a* (FIGS. 2, 8, 11)

f) along the top of cartridge 160 (through post 171 and under pin 153);

g) down along the back of cartridge 160 and around into loop 231 (held in place by loop retaining pin 165);

h) up the back and along the top of cartridge 160 in the opposite direction;

i) along the side of the tissue contacting face 166*b* of the cartridge;

j) through gap 168*p* between fastener slots 163*s* and 163*r*;

k) parallel to knife slot 169 and through region 168*o* of slot 163*r*;

l) again up along the side of the tissue contacting face 166*b* of the cartridge and around into loop 231;

m) back over the top of the cartridge, down through tissue contacting face 166*a* and through gap 167*p* between fastener slots 163*i* and 163*h*;

n) parallel to knife slot 169 and through region 167*o* of fastener slot 163*h*;

o) along the side of the tissue contacting face 166*a* of the cartridge, around into loop 231, back along the top of the cartridge and down through opposing contacting face 166*b*;

p) through gap 168*l* between fastener slots 163*p* and 163*q*;

q) through region 168*k* of slot 163*p*; and r) around the other side of the cartridge, around pin 161, and down into spool box 220 which is located on the opposite side of the cartridge from spool box 210.

Suture 238

Figure 12:
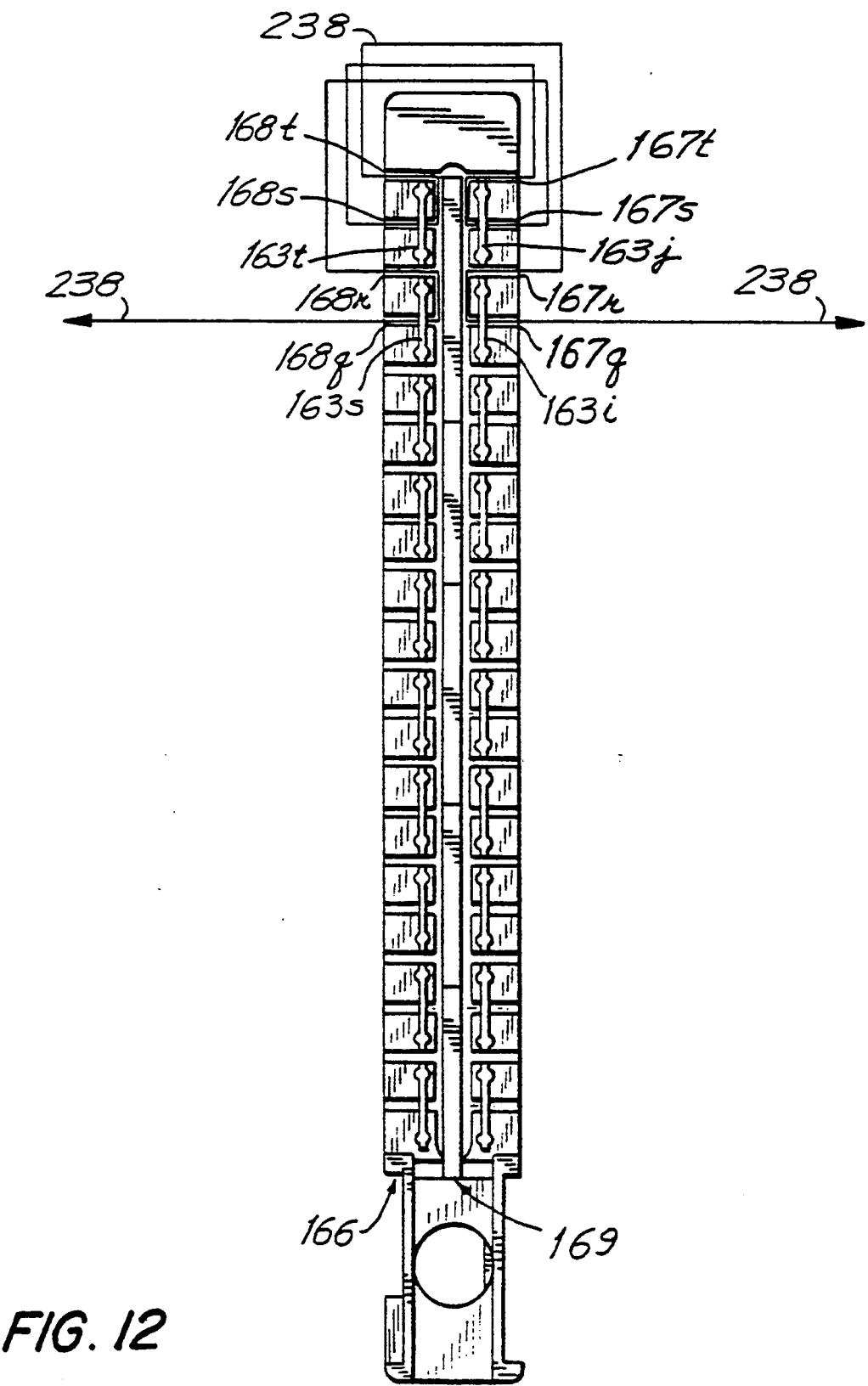

Suture 238 is positioned as follows:

a) through aperture 212*b* of spool 210 and around pin 161 (FIG. 2);

b) across the side of the cartridge and through the fastener slot 163*i* in region 167*q* (corresponding to the approximate mid portion of the backspan of the fastener portion) (FIGS. 8 and 12);

c) a short distance parallel to the central knife slot 169 of the fastener cartridge;

d) through gap 167*r* between fastener slots 163*i* and 164*j*;

e) along the side of the tissue contacting surface 166*a* (FIGS. 2, 8, 12)

f) along the top of cartridge 160 (through post 171 and under pin 153);

g) down along the back of cartridge 160 and around into loop 231 (held in place by loop retaining pin 165);

h) up the back and along the top of cartridge 166 in the opposite direction;

i) along the side of the tissue contacting face 166*b* of the cartridge;

j) through gap 168*t* between uppermost fastener slot 163*t* and the uppermost portion of the cartridge;

k) parallel to knife slot 169 and through region 168*s* of slot 163*t*;

l) again up along the side of the tissue contacting face 166*b* of the cartridge and around into loop 231;

m) back over the top of the cartridge, down through tissue contacting face 166*a* and through gap 167*t* between uppermost fastener slot 163*j* and the uppermost portion of the cartridge;

n) parallel to knife slot 169 and through region 167*s* of fastener slot 163*j*;

o) along the side of the tissue contacting face of the cartridge, around into loop 231, back along the top of the cartridge and down through opposing contacting face 166*b*;

p) through gap 168*r* between fasteners slot 168*s* and 168*t*;

q) through region 168*q* of slot 163*t*; and r) around the other side of the cartridge, around pin 161, and down into spool box 220 which is located on the opposite side of the cartridge from spool box 210.

Turning now to the operation of the apparatus, before the apparatus is fired, the tissue to be fastened is positioned in the gap between the distal leg 151 and cartridge 160. Lever 140 is pressed downwardly so that the cartridge 160 is approximated towards anvil assembly 170 to clamp the body tissue (See FIG. 3).

Figure 4B:
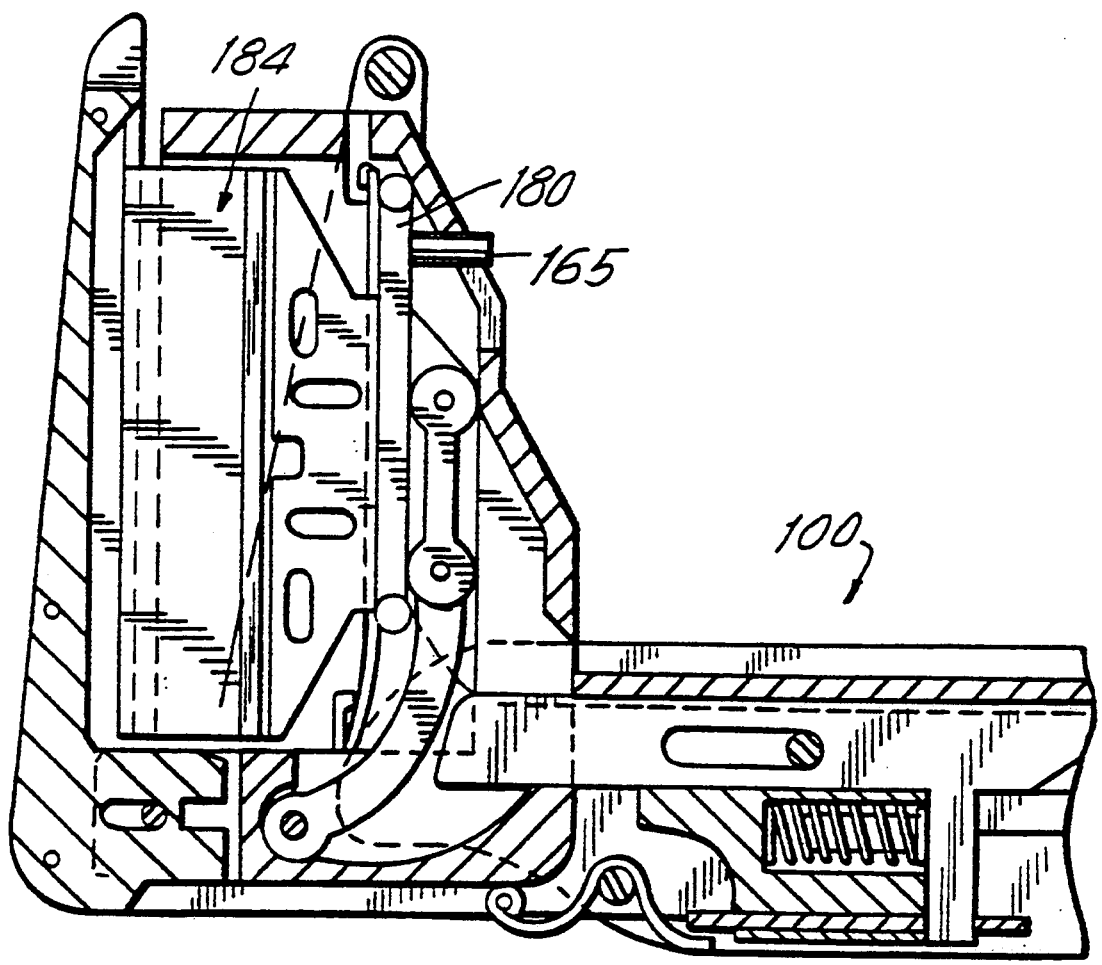

Upon squeezing of trigger 130 to fire the apparatus, the cam bar 180 is moved distally so as to apply force to the fastener pusher 182 and the knife 184 to drive out the fasteners 11 i.e. the fastener portions of the two part fasteners) and the knife 184 from their respective slots. When the cam bar 180 is moved forwardly as shown in FIGS. 4*a* and 4*b*, the loop retaining pin 165 is moved upwardly and inwardly in aperture 164 and pin 161 is moved upwardly and distally in slot 163. This movement of pin 165 releases loop 231, which is no longer held in place, i.e. tensioned, along the rear of the cartridge. The tension applied to the sutures when pin 161 is moved upwardly and forwardly is sufficient to disengage the catch members of spool boxes 210, 220 from the pins as the boxes 210, 220 are pulled upwardly along the respective sides of the cartridge. Note that in the embodiment of FIGS. 5a, 5b, firing of the apparatus pivots the loop retainer 364 distally as described above to release the suture loop of the sutures.

Figure 6:
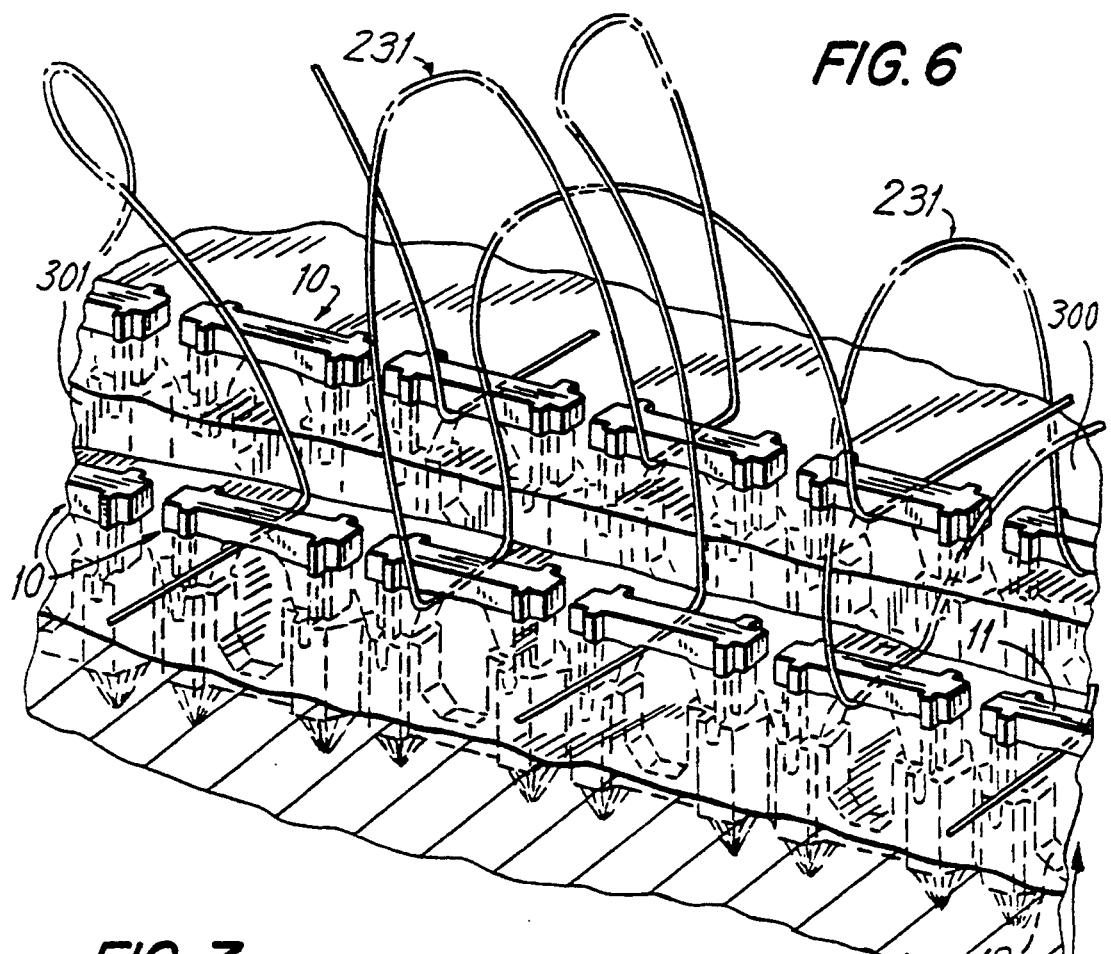
FIGS. 6 and 7 illustrate an enlarged perspective view showing several of the fasteners and a portion of the suture array of the present invention as applied to body tissue.
Figure 7:
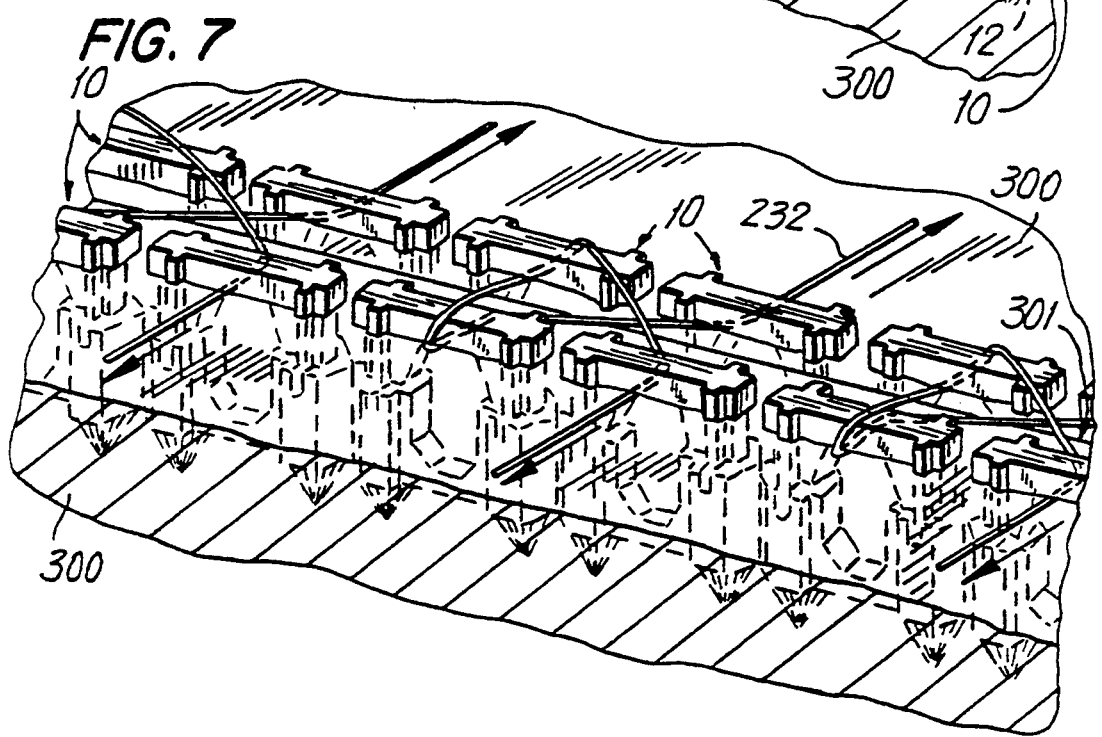

The configuration of sutures with the fired fasteners applied to tissue 300 is illustrated in FIGS. 6 and 7. As can be seen, fully engaged fasteners 10 extend in end to end fashion along two rows, one row on each side of incision 301. The sutures extend underneath the backspans of the fastener portions, between the legs of the fasteners and around into the loop 231 so as to be positioned out of the cutting line of the apparatus when fired. However, as shown in FIG. 7, when the ends of the sutures are pulled, the suture loop 231 tightens up and the edges of the incision are brought together such that the sutures are arrayed in crisscross fashion across the incision in the tissue.

Note that in the preferred embodiment, the lengths of sutures 232, 234, 236 and 238 are equal. Each suture is wrapped around its respective spool to a different degree, corresponding to the length of suture required to wind through the fasteners in the pre-fired position. For example, suture 238 wraps around spool 213b a greater amount than suture 236 wraps around spool 213d to account for the slack which would otherwise occur since suture 236 is wound along a shorter route through the fasteners than suture 236. Consequently, when the apparatus is fired, pulling the spool boxes will tension each suture sequentially, i.e. suture 232 will be tensioned first, followed by sutures 234, 236 and 238, until all four sutures are tensioned.

It should also be appreciated that a fewer or greater number of sutures can be provided to achieve the wound closure function of the present invention. Moreover, the sutures can be threaded through the fasteners and connected to the cartridge in other ways than those described above and sutures of different sizes can be provided. The sutures may also be color coded to facilitate identification of the two suture ends.

Figure 13:
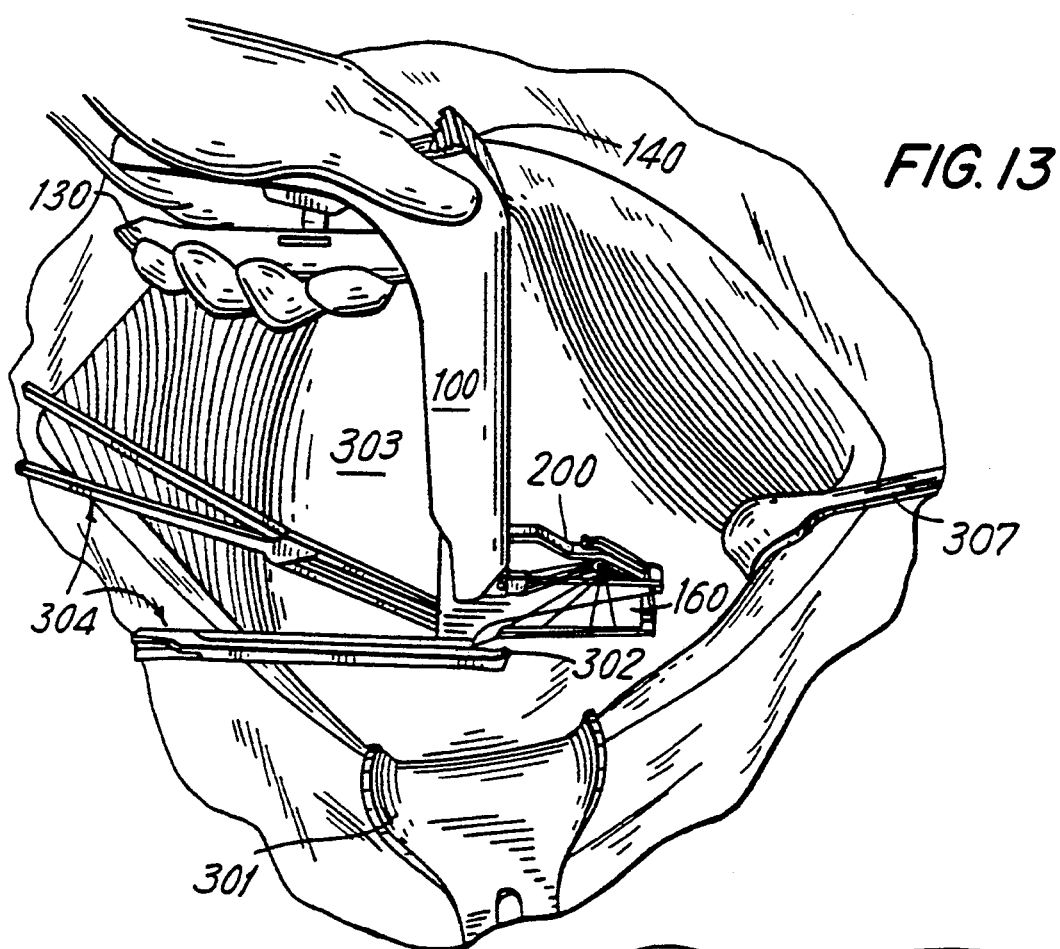
FIGS. 13, 14, 15 and 16 sequentially illustrate a surgical operation employing the apparatus of the present invention.

FIGS. 13, 14, 15 and 16 illustrate a hysterotomy such as is performed during a cesarean section using the instrument of the present invention. To perform the cesarean section in accordance with the method of the present invention, the abdomen of the patient is cut and the peritoneal muscle tissue is incised to create a bladder flap. Retractors 301 may be used to facilitate access to the uterus. A small (about 1 cm.) lateral incision 302 is made in the uterus 303 with care to avoid rupture of the amniotic sac. A finger is then inserted to clear away fetal tissue from the area to be stapled. Allis clamps 304 may be placed along the edges of the uterine incision to assist in stabilizing the uterus. The apparatus 100 is inserted through incision 302 as shown in FIG. 13, the cartridge 160 is approximated to the uterine tissue by pressing lever 140 into position as shown, and the trigger 130 is squeezed to fire the instrument. When the apparatus 100 is opened and withdrawn, the suture array assembly 200 remains behind in conjunction with the applied fasteners 10.

Figure 14:
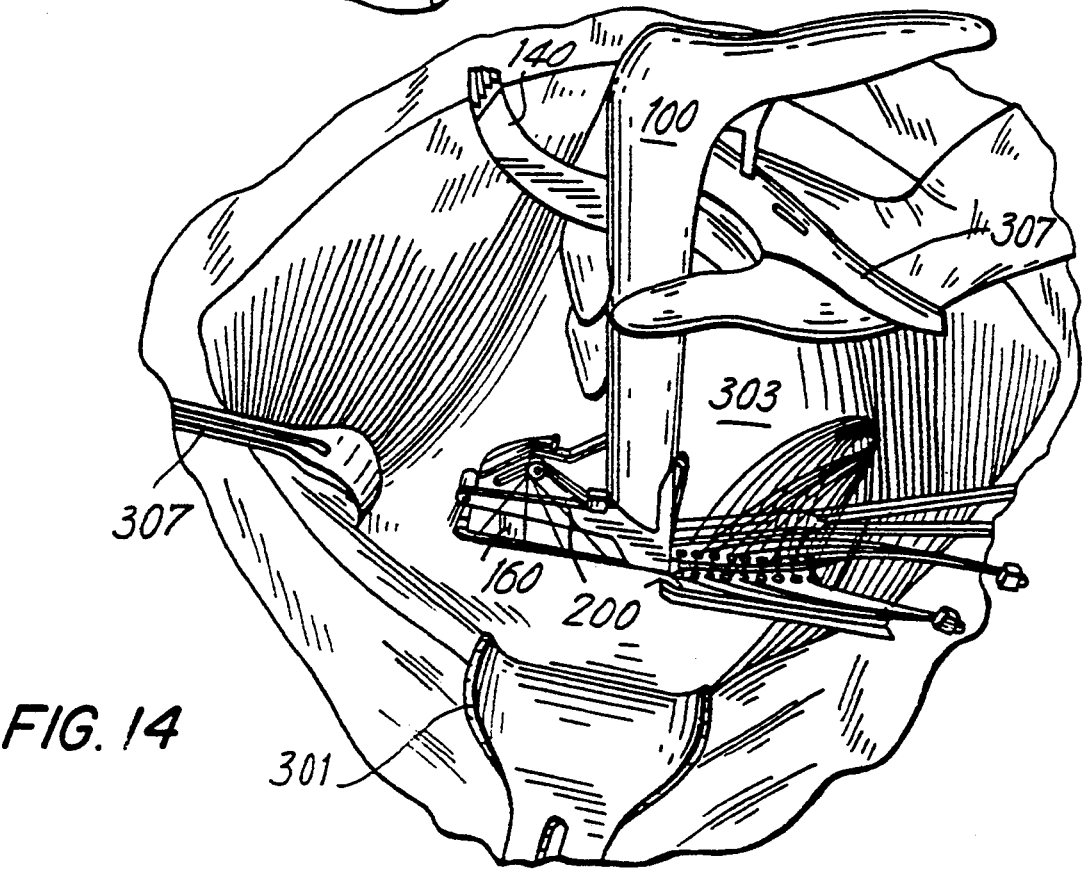
Figure 16:
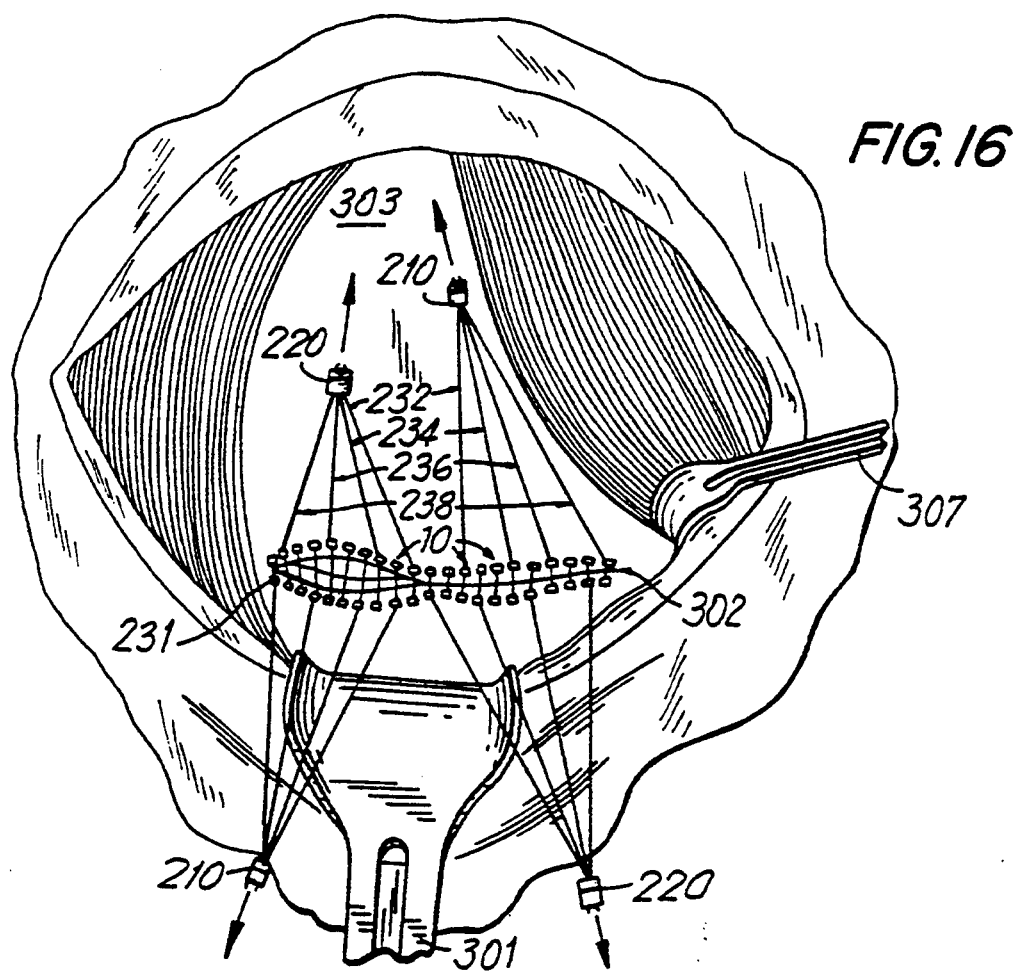

The same procedure is repeated with a fresh apparatus on the other side of the uterus as shown in FIG. 14.

Figure 15:
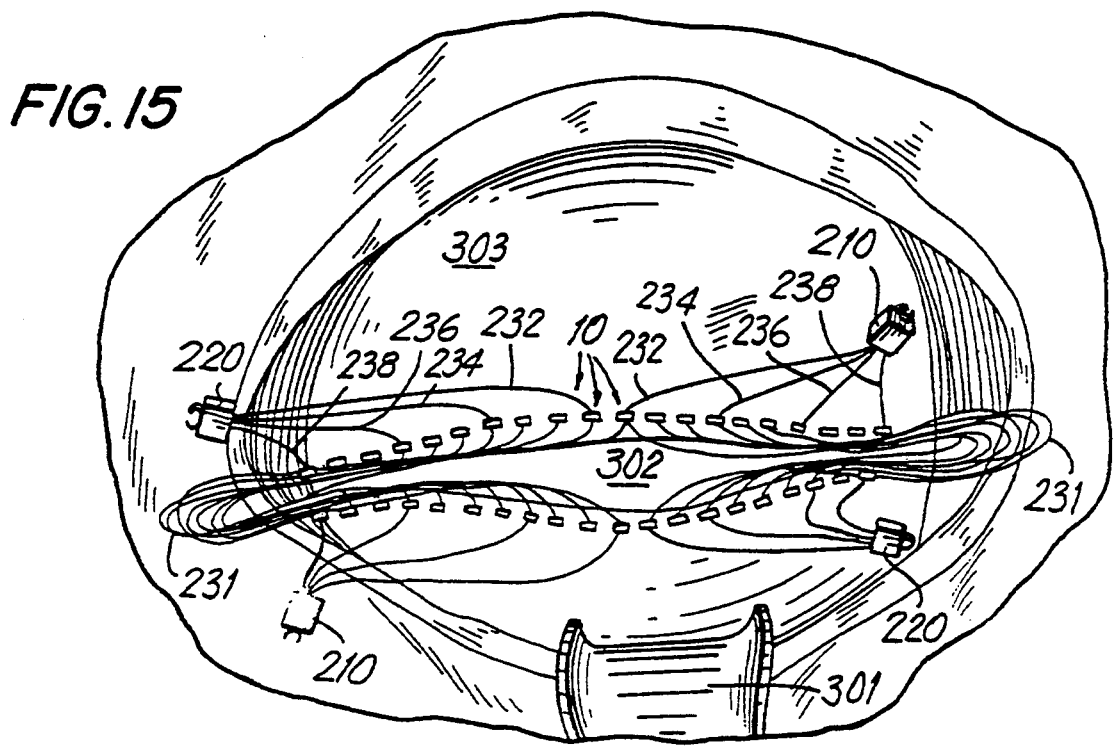

The resulting simultaneous application of sutures and fasteners is shown in FIG. 15. The baby is delivered through incision 302, with the tissue 300 at the edge of the incision 302 sealed and hemostasis is achieved by the rows of fasteners 10 on both sides of the incision.

After the delivery, the surgeon closes the incision by pulling the opposing spool boxes 210, 220, thereby reducing the loops 231 and drawing the edges of the tissue together into close contact to close incision 302. The spool boxes are cut away from the sutures by means of a scissor or other cutting instrument the sutures tied off to prevent loosening. Thereafter, the procedure is concluded in the usual manner by stitching the incisions in the peritoneal tissue and abdominal skin.

The simplicity of closing the uterine incision with the suture array of the present invention, as contrasted with the prior known method, is advantageous insofar as operating time, blood loss and trauma are even further reduced.

What is claimed is:

1. A surgical fastener applying apparatus for applying a plurality of surgical fasteners comprising:
   a frame;
   a plurality of surgical fasteners, each of the individual fasteners having a backspan and a pair of legs extending therefrom, each backspan having a longitudinal axis extending therethrough;
   means mounted to said frame for holding the plurality of surgical fasteners in at least two rows, such that the individual fasteners in each row are oriented in end to end fashion with the longitudinal axes of the backspans in each row in substantial alignment,
   at least one suture cooperating with at least one of said surgical fasteners; and
   means for applying said surgical fasteners to body tissue, said applying means applying said at least one suture in conjunction with said fasteners, a portion of said at least one suture extending across the rows from a fastener on one of said rows to a fastener on another of said rows.

2. The surgical fastener applying apparatus of claim 1, wherein said fasteners are fabricated from a bioabsorbable material.

3. The surgical fastener applying apparatus of claim 2, wherein said bioabsorbable material is selected from the group consisting of homopolymers and copolymers of glycolide, lactide, dioxanone, caprolactone, trimethylene carbonate and blends thereof.

4. The surgical fastener applying apparatus of claim 1, wherein said at least one suture is fabricated from a bioabsorbable material.

5. The surgical fastener applying apparatus of claim 4, wherein said bioabsorbable material is selected from the group consisting of homopolymers and copolymers of glycolide, lactide, dioxanone, caprolactone, trimethylene carbonate and blends thereof.

6. The surgical fastener applying apparatus of claim 1, wherein said fasteners are two-part fasteners.

7. The surgical fastener applying apparatus of claim 1, wherein said fasteners are metal staples.

8. The surgical fastener applying apparatus of claim 1, wherein said means for holding the fasteners includes a tissue contacting face, said portion of said suture extending across the rows being at least partially positioned in a loop located away from said tissue contacting face.

9. The surgical fastener applying apparatus of claim 8, wherein said apparatus further includes means for releasably holding said loop until said fasteners are applied.

10. The surgical fastener applying apparatus of claim 1, wherein said apparatus includes four sutures.

11. The surgical fastener applying apparatus of claim 10, wherein said four sutures are of substantially the same length.

12. The surgical fastener applying apparatus of claim 1, further including anchoring means for holding each end of said at least one suture.

13. The surgical fastener applying apparatus of claim 12, wherein said anchoring means includes at least one housing, and at least one tensioned rotatable spool located in said housing for each end of said suture.

14. The surgical fastener applying apparatus of claim 13, wherein said housing is releasably mounted to said frame of said apparatus, said housing being releasable upon actuation of said means for applying said surgical fasteners.

15. A surgical fastener applying apparatus for applying a plurality of surgical fasteners, each fastener having a backspan comprising:
a frame;
a fastener holding member on said frame for holding the plurality of surgical fasteners in at least first and second rows, such that the backspan of each fastener is oriented in a direction perpendicular to a longitudinal axis of said frame;
at least one suture cooperating with at least one of said surgical fasteners in said first row and said second row; and
a pusher for applying the surgical fasteners to body tissue in conjunction with said at least one suture.

16. The surgical fastener applying apparatus of claim 15, wherein a portion of said at least one suture extends in a first path from a fastener on said first row to a fastener on said second row and further extends in a second path to another fastener on said first row.

17. The surgical fastener applying apparatus of claim 16, wherein said pusher for applying surgical fasteners is configured to apply the fasteners and said at least one suture substantially simultaneously.

18. The surgical fastener applying apparatus of claim 16, further including anchoring means on said frame for holding each end of said at least one suture.

19. The surgical fastener applying apparatus of claim 18, wherein said anchoring means includes at least one housing, and at least one tensioned rotatable spool located in said housing for each end of said suture.

20. The surgical fastener applying apparatus of claim 19, wherein said housing is releasably mounted to said frame of said apparatus, said housing being releasable upon actuation of said means for applying said surgical fasteners.

21. In a surgical fastener applying apparatus for applying two-part surgical fasteners to body tissue, the apparatus having a longitudinal axis and said two part surgical fasteners each comprising a fastener portion and a retainer portion engageable with said fastener portion, the fastener portion having a backspan and a pair of legs extending therefrom, the backspans of the fasteners being positioned generally transverse to the longitudinal axis and the legs extending in a direction substantially parallel to the longitudinal axis, the improvement comprising means for simultaneously applying at least one suture to said body tissue in conjunction with said fasteners.

22. The surgical fastener applying apparatus of claim 21, wherein said apparatus includes four sutures and said applying means applies said four sutures substantially simultaneously.

23. The surgical fastener applying apparatus of claim 22, wherein said four sutures are of substantially the same length.

24. The surgical fastener applying apparatus if claim 21, further including anchoring means on a frame of the apparatus for holding each end of said at least one suture.

25. The surgical fastener applying apparatus of claim 24, wherein said anchoring means includes at least one housing, and at least one tensioned rotatable spool located in said housing for each end of said suture.

26. The surgical fastener applying apparatus of claim 21, wherein said two part fasteners are bioabsorbable.

27. A surgical fastener applying apparatus for applying a plurality of fasteners comprising:
a cutting member for making an incision in body tissue;
a holding member for holding at least one row of surgical fasteners on each side of said cutting member;
at least one surgical suture cooperating with at least one of said surgical fasteners; and
means cooperating with said fasteners for substantially simultaneously applying said at least one suture and said at least one row of surgical fasteners on each side of said incision.

28. The surgical fastener applying apparatus of claim 27, wherein said applying means applies said at least one suture such that a portion of said at least one surgical suture extends from a fastener on one side of said incision to a fastener on the other side of said incision.

29. A surgical fastener applying apparatus of claim 28, wherein said apparatus comprises four sutures.

30. A surgical fastener applying apparatus for closing an opening in the body tissue comprising:
means for closing an opening in body tissue, said closing means including a plurality of fasteners and at least one suture cooperating with at least one of said fasteners; and;
actuating means for firing said fasteners to apply said fasteners and said at least one suture to the body tissue, said fasteners being applied on oppposing sides of the opening and said suture extending across said opening.

31. The surgical fastener applying apparatus of claim 30, wherein said actuating means includes a first handle movably connected to a second stationary handle.

32. The surgical fastener applying apparatus of claim 30, wherein said fasteners and said at least one suture are applied to the body tissue substantially simultaneously.

33. The surgical fastener applying apparatus of claim 32, wherein said apparatus further comprises a frame and a cartridge mounted to said frame, said cartridge retaining said fastener and said at least one suture.

34. The surgical fastener applying apparatus of claim 33, wherein said apparatus includes four sutures.

35. The surgical fastener applying apparatus of claim 33, further comprising an anchor mounted to said frame, said anchor retaining an end of said at least one suture.

36. A surgical fastener applying apparatus of claim 35, wherein said anchor comprises a spool, said spool disposed within a housing releasably mounted to said frame.

37. A surgical fastener applying apparatus of claim 36, wherein said cartridge includes a slot to slidably receive a mounting pin, said mounting pin retaining a looped end of said least one suture.

38. A surgical fastener applying apparatus of claim 30, wherein said fasteners are two part fasteners comprised of a bioabsorbable material.

39. A surgical fastener applying apparatus of claim 38, further comprising a knife, said knife creating an incision in body tissue upon actuation of said actuating means.

40. A cartridge for use in a surgical fastener applying apparatus for applying a plurality of surgical fasteners arranged in at least first and second rows, the apparatus adapted to receive said cartridge, said cartridge comprising:
  means for holding a plurality of surgical fasteners;
  pusher means for driving the fasteners from said cartridge through respective fastener exit apertures in a tissue contacting distal face of said cartridge; and
  at least two sutures releasably mounted to said cartridge, each suture having a portion extending across at least one of said fastener exit apertures in said first row and a portion extending across at least one of said fastener exit apertures in said second row.

41. The cartridge of claim 40 where, a portion of said suture between the, said first and second rows extends in a loop positioned away from said tissue contacting distal face.

42. The cartridge of claim 41, further comprising means for releasably holding said loop until said pusher means is actuated.

43. A surgical fastener applying apparatus comprising:
  a frame having a longitudinal axis;
  a fastener cartridge containing at least one fastener and at least one suture;
  a pair of jaws, one of said jaws having means for receiving said fastener cartridge;
  means for moving at least one of said jaws along said longitudinal axis from an open position to a closed position to clamp tissue therebetween; and
  means for applying said at least one fastener and said at least one suture to body tissue, said at least one fastener being applied in a direction substantially parallel to said longitudinal axis.

44. The surgical fastener applying apparatus of claim 43, wherein said applying means is configured to apply said at least one surgical fastener and said at least one suture substantially simultaneously and in conjunction with each other.

45. The surgical fastener applying apparatus of claim 44, further comprising means for cutting body tissue, said cutting means actuated by movement of said fastener applying means.

46. The surgical fastener applying apparatus of claim 43, wherein said apparatus applies four sutures.

47. The surgical fastener applying apparatus of claim 43, wherein said fasteners are two part fasteners composed of a tissue piercing portion and a receiving portion.

48. The surgical fastener applying apparatus of claim 47, wherein said at least one suture extends between said tissue piercing portion and said respective receiving portion when said fasteners are applied to body tissue.

49. The surgical fastener applying apparatus of claim 48, further comprising four sutures, each suture passing between a different tissue piercing portion and respective receiving portion.

50. The surgical fastener applying apparatus of claim 49, further comprising a frame for mounting said fastener cartridge, said cartridge having a member for retaining said at least one suture.

51. The surgical fastener applying apparatus of claim 50, wherein said retaining member comprises a housing having at least one spool for holding said sutures, said housing releasably mounted to said frame.

52. The surgical fastener applying apparatus of claim 50, comprising a number of spools, said sutures being initially wrapped around said respective spool to a different degree.

53. The surgical fastener applying apparatus of claim 50, further comprising slidable anchor means mounted on said frame for holding a looped end of said sutures.

54. A surgical fastener applying apparatus for applying a plurality of surgical fasteners for closing an opening in body tissue comprising:
  a frame;
  a first member on said frame for holding at least two opposing rows of surgical fasteners;
  connecting means cooperating with at least one of said fasteners in each of said rows of surgical fasteners; and
  a pusher for applying said at least two rows of fasteners and said connecting means such that said connecting means is applied in a direction and orientation with respect to said fasteners such that application of tension to said connecting means moves said opposing rows of fasteners toward each other.

55. The surgical fastener applying apparatus of claim 54, wherein said connecting means comprises at least one suture.

56. A cartridge for use in a surgical fastener applying apparatus adapted to receive said cartridge comprising:
  a plurality of surgical fasteners;
  means for holding the plurality of surgical fasteners in at least two rows;
  pusher means for driving said fasteners from said cartridge through respective fastener exit apertures in a tissue contacting distal face of said cartridge;
  at least one suture releasably mounted to said cartridge and having a portion extending across at least one of said fastener exit apertures in one row and a portion extending across at least one of said fastener exit apertures in the other of said rows; and
  said suture extending in a first path from a fastener in said first row to a fastener in said second row and in a second path from said fastener in said second row to another fastener in said first row.

57. The cartridge of claim 56, wherein said fasteners are two part fasteners comprising a tissue piercing portion and a retainer portion.

58. The cartridge of claim 57, further comprising a cutting member, said two part fasteners being arranged in at least two parallel rows and said cutting member is positioned between said rows of fasteners.

59. A method for performing a cesarean section operation, comprising:
  a) making at least one incision in uterine tissue;
  b) substantially simultaneously applying 1) at least one row of surgical fasteners to said tissue when making said incision; and 2) at least one suture to the body tissue when applying said fasteners, c) bringing the sides of the incision into approximation for closure thereof by pulling ends of said at least one suture.

60. The method of claim 59, wherein said suture has two ends, a first portion engaged by a fastener on one of said rows, a second portion engaged by a fastener on the other of said rows, and a loop portion extending around the location of said incision, said loop being reducible when said suture ends are pulled for closing said incision.

61. A method for closing an opening in body tissue comprising:

a) approximating a first instrument jaw toward a second instrument jaw to clamp body tissue therebetween;

b) substantially simultaneously applying at least one row of fasteners to the body tissue on each side of the opening, and at least one suture, at least a portion of said suture extending from a row of said fasteners on one side of the opening to a row on the other side of said opening; and, c) tightening said at least one suture to close the opening in the body tissue.

62. The method of claim 61, wherein said fasteners are two-part bioabsorbable fasteners.

63. The method of claim 62, wherein the fasteners within a row are oriented in end to end fashion.

* * * * *